United States Patent
Baba et al.

(10) Patent No.: US 8,420,891 B2
(45) Date of Patent: Apr. 16, 2013

(54) METHOD FOR INTRODUCING FOREIGN SUBSTANCE INTO CELL HAVING CELL WALL

(75) Inventors: Yoshinobu Baba, Nagoya (JP); Manabu Tokeshi, Nagoya (JP); Noritada Kaji, Nagoya (JP); Ibrahim Maged Fouad Serag Eldin Bayoumi, Nagoya (JP)

(73) Assignee: National University Corporation Nagoya University, Aichi (JP)

( * ) Notice: Subject to any disclaimer, the term of this patent is extended or adjusted under 35 U.S.C. 154(b) by 385 days.

(21) Appl. No.: 12/665,186

(22) PCT Filed: Jun. 11, 2008

(86) PCT No.: PCT/JP2008/060689
§ 371 (c)(1),
(2), (4) Date: Dec. 17, 2009

(87) PCT Pub. No.: WO2008/156021
PCT Pub. Date: Dec. 24, 2008

(65) Prior Publication Data
US 2010/0248373 A1  Sep. 30, 2010

(30) Foreign Application Priority Data
Jun. 21, 2007  (JP) .................................. 2007-163867

(51) Int. Cl.
*C12N 15/82* (2006.01)
*C12N 15/56* (2006.01)
*C12N 15/87* (2006.01)
*C12N 11/04* (2006.01)

(52) U.S. Cl.
USPC ........... 800/293; 435/180; 435/182; 435/209; 435/470

(58) Field of Classification Search ........................ None
See application file for complete search history.

(56) References Cited

U.S. PATENT DOCUMENTS 7,132,289 B2  11/2006  Kobayashi et al.
7,838,273 B2 *  11/2010  Kim ............................... 435/176

FOREIGN PATENT DOCUMENTS

JP  2002-325572  11/2002
WO  2006/130150  12/2006

OTHER PUBLICATIONS

International Search Report for PCT/JP2008/060689 mailed on Aug. 12, 2008.
Extended European Search Report for European Application No. 08765468.7 mailed on Jul. 2, 2010.
Rojas-Chapana, et al. Multi-walled carbon nanotubes for plasmid delivery into *Escherichia coli* cells, Lab on a Chip, vol. 5, pp. 536-539, 2005.
Klumpp, et al. Functionalized carbon nanotubes as emerging nanovectors for the delivery of therapeutics, Biochimica Et Biophysica Acta, vol. 1758, pp. 404-412, 2006.
Torney, et al. Mesoporous silica nanoparticles deliver DNA and chemicals into plants, Nnano.2007.108, vol. 2, pp. 295-300, May 2007.
European Office Action for European Application No. 08765468.7 mailed on Aug. 9, 2012.

* cited by examiner

*Primary Examiner* — David T Fox
(74) *Attorney, Agent, or Firm* — Turocy & Watson, LLP

(57) ABSTRACT

Disclosed is a method for introducing a foreign substance (3) into a cell (1) having a cell wall. The method comprises the steps of: providing a carbon nanotube (2) carrying at least one enzyme capable of decomposing a cell wall; supplying the carbon nanotube (2) and the foreign substance (3) into a treatment solution containing the cell (1); decomposing the cell wall of the cell (1) by the action of the enzyme carried on the carbon nanotube (2) upon the contact of the carbon nanotube (2) with the cell (1); and introducing the foreign substance (3) into the cell (1) through a site decomposed with the enzyme on the cell wall.

7 Claims, 6 Drawing Sheets

5 μm

20 μm

20 μm

20 μm

20 μm

METHOD FOR INTRODUCING FOREIGN SUBSTANCE INTO CELL HAVING CELL WALL

CROSS-REFERENCES TO RELATED APPLICATIONS

This application claims priority under 35 USC 371 to International Application No. PCT/JP2008/060689, filed Jun. 11, 2008.

The priority claim for this international application is based on Japanese Patent Application No. 2007-163867 filed on Jun. 21, 2007, and the entire content of that application is incorporated by reference in this Specification.

TECHNICAL FIELD

The present invention relates to a method for introducing a nucleic acid (DNA, RNA), protein or other foreign substance into a cell having a cell wall. In particular, this invention relates to a foreign substance introduction method using a carbon nanotube.

BACKGROUND ART

Various methods are known for introducing DNA, RNA and other polynucleotides and proteins, lipids and other biological substances as foreign substances into target cells. For example, methods that are known for introducing DNA and other genetic material include methods using liposomes (lipofection methods), microinjections methods, electroporation methods, methods using virus vectors, DEAE-dextran transfection, methods using gene guns and the like.

However, it is generally more difficult to introduce foreign substances into plant cells than into animal cells. A plant cell is enveloped by a tough cell wall containing cellulose, and this cell wall presents a barrier to introduction of foreign substances. A common way of increasing the introduction rate of foreign substances into cells is to treat the cells in advance with an enzyme (such as cellulase), converting them into protoplasts. However, the protoplast conversion is a difficult and complex operation. Moreover, skill and care are required when handling cells that have been converted to protoplasts.

One example of this kind of prior art is given in Patent Document 1, which describes using the high working characteristics of laser light to break the polymeric chemical bonds composing the plant cell wall so that a gene or other foreign substance (biological substance) can be introduced into a plant cell. However, the method described in this document still requires an expensive laser irradiation mechanism, and involves complex and difficult operations (laser irradiation treatment, etc.).

Patent Document 1: Japanese Patent Application Laid-open No. 2002-325572

DISCLOSURE OF THE INVENTION

The present invention was created to resolve the problems of prior art with respect to introduction of foreign substances (for example biological substances, especially DNA and other genetic material) into plant cells and other cells having cell walls, and it is an object of the present invention to provide a convenient and easy method for introducing foreign substances into target cells. In particular, it is an object of the present invention to provide an introduction method capable of easily and efficiently introducing DNA, RNA or other genetic material (typical exogenous genes) into target cells.

In order to resolve these problems, the method provided by the present invention is a method for introducing a foreign substance into a cell having a cell wall. The method disclosed here comprises the steps of: preparing a carbon nanotube carrying at least one cell wall-decomposing enzyme; supplying the cell wall-decomposing enzyme-carrying nanotube and a foreign substance to be introduced to a treatment object containing the cell (typically a treatment solution containing the cell); decomposing the cell wall of the cell by an action of the decomposing enzyme carried on the carbon nanotube upon contact of the carbon nanotube with the cell; and introducing the target foreign substance into the cell through the decomposed site on the cell wall.

In this Description, a "foreign substance (introduced substance)" is a substance whose size and properties are such that it can be supplied inside the target cell. It may be a naturally occurring substance or an artificially manufactured substance. Typical examples include various biological molecules. For example, polynucleotides (DNA, RNA), polypeptides, proteins and other biological molecules are included here as desirable examples of foreign substances (introduced substances).

In this Description, a "carbon nanotube" is a structure consisting of a carbon framework, and is a tubular or fibrous carbon structure with a diameter on the order of nanometers (typically 200 nm or less, for example 1 to 200 nm) consisting of a single layer or multiple rolled layers. In addition to so-called single-walled carbon nanotubes (SWNT) and multi-walled carbon nanotubes (MWNT), those called carbon nanofibers (carbon nanowhiskers) and carbon nanohorns because of their structural characteristics are also considered carbon nanotubes in the context of this Description.

By using a carbon nanotube with the desired cell wall decomposing-enzyme fixed thereon, it is possible to open a tiny hole (nano-hole) in the cell wall of a target cell by the action of the cell wall-decomposing enzyme fixed on the carbon nanotube in the foreign substance introduction method of the present invention. Hence, the introduction of the target foreign substance into the cell from this nano-hole is enabled.

Because the hole formed in the cell wall of the target cell by this method is extremely small, moreover, the post-treatment cell survival rate is extremely high (in other words, self-recovery from perforation occurs easily after introduction treatment), and it is possible to obtain normal cells (non-defective cells) that retain their intrinsic functions. In addition, special care is not required in handling the cells. Consequently, with the present invention it is possible to efficiently obtain a cell with a foreign substance introduced therein with high efficiency and without any complex or bothersome operations.

Thus, another aspect of the present invention provides a method for producing a transformed cell (as well as tissue produced from such a transformed cell) having a foreign substance introduced therein, wherein a polynucleotide (which may be a gene consisting of DNA or RNA, a vector containing such a gene, or a complex of a polynucleotide with another substances (such as a protein)) is introduced into a target cell as a foreign substance by the introduction method of the present invention.

A preferred embodiment of the method disclosed here uses at least one kind of cellulase as the aforementioned enzyme.

By using cellulase, it is possible to effectively form a small hole in the wall of a target cell, particularly a plant cell.

Consequently, in cases in which the cell is a plant cell in particular it is preferable to fix a cellulase on the carbon nanotube.

In another preferred embodiment of the method disclosed here, a carbon nanotube with a total (average) length of 10 μm or less is used as the carbon nanotube.

By using such a relatively short carbon nanotube as the carbon nanotube, it is possible to improve the random mobility (typically Brownian motion such as translation and rotation) of the anisotropic carbon nanotube particles in the treatment liquid, resulting in more frequent contact with the target cells and more efficient perforation of the cell walls by the enzyme fixed on the carbon nanotubes, and consequently in more efficient introduction of the foreign substance.

In another preferred embodiment of the method disclosed here, the prepared cell wall decomposing enzyme-carrying carbon nanotubes are first added to a solution containing a surfactant (preferably a nonionic surfactant and/or cationic surfactant) to prepare a solution for foreign substance introduction, and this prepared solution is then supplied to a treatment object containing the cells.

By adding the cell wall degrading enzyme-carrying carbon nanotubes to a solution containing a surfactant (preferably a nonionic surfactant and/or cationic surfactant) to prepare a solution for foreign substance introduction before supplying them to a treatment object containing the target cells, and then using the prepared solution, it is possible to further promote the random action of the carbon nanotubes carrying the cell wall-decomposing enzyme. Perforation of the cell walls of the target cells is also promoted, thereby further increasing the introduction efficiency of the foreign substance. The desired foreign substance can also be added to this solution for foreign substance introduction in addition to the cell wall-decomposing enzyme-carrying nanotubes.

Preferably the cell treatment object is a treatment solution containing the cells, and this cell treatment solution contains a surfactant, especially a nonionic surfactant and/or cationic surfactant. More preferably, n-octyl-β-D-glucoside is used as the nonionic surfactant. Including this surfactant in the treatment solution serves to both promote the random motion of the carbon nanotubes in the treatment solution and to improve the introduction efficiency of the foreign substance (particularly a polynucleotide such as DNA or RNA).

The present invention also provides a cell having a specific foreign substance introduced into the cell by the method disclosed here. A plant cell (and also a tissue or plant body obtained from this plant cell) in particular can be provided as a desirable example. Typically a cell is provided having a cell wall-decomposing enzyme-carrying carbon nanotube introduced (incorporated) into the cell together with the specific foreign substance.

The present invention also provides a combination of materials for favorably implementing the foreign substance introduction method disclosed here, or in other words a kit for introducing a foreign substance into a plant cell or other cell having a cell wall.

The foreign substance introduction kit provided by the present invention comprises at least one kind of cell wall decomposing enzyme, carbon nanotubes, and a solution for foreign substance introduction containing at least one kind of surfactant (preferably a nonionic surfactant and/or cationic surfactant).

In a preferred embodiment of the kit, the at least one kind of cell wall decomposing enzyme is already carried on the carbon nanotubes contained in the kit.

With the kit provided by the present invention, it is easy to prepare the aforementioned solution for foreign substance introduction, and easy for the cell wall-decomposing enzyme carried on the carbon nanotubes to contact the cells and decompose the cell walls so that the target foreign substance can be introduced into the cells through the decomposed sites on the cell walls.

In a preferred embodiment of the kit, the enzyme is at least one kind of cellulase. In another preferred embodiment of the kit, the nonionic surfactant is n-octyl-β-D-glucoside.

Using this kit, a cell wall-decomposing enzyme-carrying carbon nanotube can be favorably introduced together with a specific foreign substance into a cell having a cell wall (typically a plant cell) by a simple operation.

BEST MODE FOR CARRYING OUT THE INVENTION

Figure 1A:
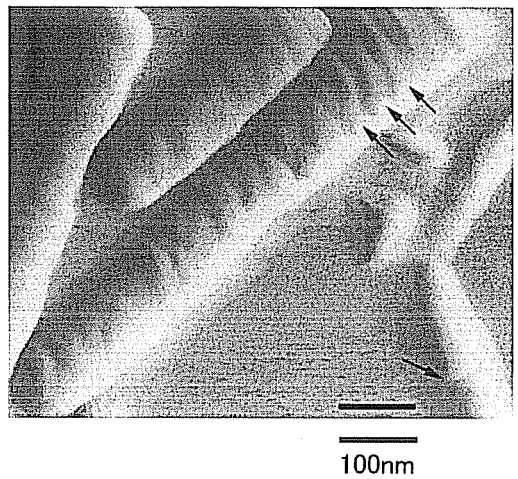
FIG. 1A is a photomicrograph showing the structure of a carbon nanotube used in one example.

Favorable examples of the present invention are explained below. Matters necessary for implementing the present invention (such as preparation methods and means of supplying the desired foreign substance) other than those matters specially mentioned in the description (for example, the method of manufacturing the carbon nanotube carrying the cell wall-decomposing enzyme or the method of supplying the carbon nanotube to a treatment object (typically a cell-containing treatment solution) containing the target cell) can be understood as design matters by a person skilled in the art based on prior art in the field. The present invention can be implemented based on the content disclosed in this Description and on technical common knowledge in the field.

As discussed above, the method disclosed herein features the supplying of a foreign substance to target cells together with carbon nanotubes carrying a suitable cell wall-decomposing enzyme, and the properties of the carbon nanotubes used, the type of cell wall-decomposing enzyme, the type of target cells, the configuration of the treatment object (e.g., the composition of the treatment solution) and the composition of the medium (specifically, the medium for culturing the cells before introduction treatment of the present invention and the media for culturing the treatment solution and cells before treatment) are not particularly limited as long as the object of the present invention is achieved.

A variety of cells having cell walls can be used as the target cells for applying the present invention, or in other words the "cells having cell walls". The cell walls of higher plants are composed of tiny fibers of cellulose interspersed with a polysaccharide matrix of pectin or hemicellulose. The cell walls of bacteria are composed primarily of peptidoglycans. The cell walls of filamentous fungi are composed primarily of β-1,3-glucans. Consequently, the cell wall-decomposing enzyme will differ depending on the target cells.

Examples of cell wall-decomposing enzymes that can be used favorably in implementing the present invention include cellulase (which catabolizes cellulose), pectinase (which catabolizes pectin), hemicellulase (which catabolizes hemicellulose), chitinase (which catabolizes chitin), β-1,3-glucanase (which catabolizes β-1,3-glucan), lysozyme (which catabolizes the cell walls of bacteria) and the like.

In a preferred embodiment of the present invention, the target cells are plant cells (typically higher plant cells), which are not well adapted to conventional introduction methods as described above.

There are no particular limits on the form in which the target cells are present in the treatment object that is treated in the present invention. Typically the treatment object (treatment solution) is a cell suspension, but the treatment solution may also contain partial tissue of plant (for example leaves, roots, stalks, seeds, pollen, petals or callus). Moreover, the "treatment object containing target cells" in this Description also encompasses a part of a plant body to which a treatment solution (that is, a solution containing carbon nanotubes and a foreign substance) has been applied as water drops, or part of a plant body that has been immersed in such a treatment solution.

When the target cells are plant cells, it is particularly desirable to use cellulase as the cell wall-decomposing enzyme. Any kind of cellulase can be used without particular limitations as long as it is an enzyme that hydrolyzes the glycoside bonds of β-1,4-glucan (cellulose), but (EC 3.2.1.4), which acts as an endoglucanase, is particularly desirable. A cellulase that acts as an endoglucanase can also be used in combination with a cellulase that acts as an exoglucanase (cellobiohydrolase: EC 3.2.1.91).

The origin of the cellulase is not particularly limited, and a commercially available cellulase can be used. For example a refined cellulase product produced by filamentous fungi (Aspergillus or the like) can be purchased and used.

The properties and production method of the carbon nanotubes are not particularly limited. SWNT, MWNT or the like may be used. From the standpoint of achieving random and active movement in the treatment solution so as to improve frequency of contact with the target cells, nanotubes with relatively short total lengths (chain lengths) are preferred. For example, short-chain carbon nanotubes having a total (average) length of 10 µm or less or more preferably a total (average) length of 5 µm or less (such as 0.1 µm to 5 µm) are preferred. Short-chain carbon nanotubes with a total (average) length of 1 µm or less (for example, 0.1 µm to 1 µm) are especially preferred. The diameter is not particularly limited but is preferably 200 nm or less, such as about 1 to 200 nm.

A metal (catalytic) fine particle is used as the growth nucleus of such a short-chain carbon nanotube, which is preferably manufactured by chemical vapor deposition (CVD) using a hydrocarbon or other carbon-containing gas as the material. A carbon nanotube obtained by this method is highly oriented, which is desirable from the standpoint of preparing large quantities of carbon nanotubes with a relatively uniform appearance and the same morphologies and properties. Therefore, short-chain carbon nanotubes manufactured by chemical vapor deposition (CVD) can be used favorably in implementing the present invention. For example, the multilayer carbon nanotubes with relatively short chain lengths known under the trade name Carbere® (GSI Creos), which are formed from stacked structures similar to open-bottomed cups, can be used by preference. Relatively short carbon nanotubes of this type are desirable for implementing the present invention because they undergo random and active translational movement (shifts in position) and rotational movement in the treatment solution.

The cellulase or other cell wall-decomposing enzyme can be carried (fixed) on the carbon nanotubes by a commonly used conventional method. For example, the enzyme can be fixed on the surface of the carbon nanotubes by adding the carbon nanotubes to an enzyme solution. Preferably, the carbon nanotubes can be subjected to acid treatment, ozone treatment, plasma treatment, heat treatment or the like to acidify the surface of the carbon nanotubes and generate various functional groups (such as carboxyl or hydroxyl groups) on the surface of the nanotubes. In this way, the cellulase or other cell wall-decomposing enzyme can be chemically bound to the carbon nanotubes by means of these functional groups. The method of introducing the functional groups on the carbon nanotubes may be a well-known conventional method (acid treatment, plasma treatment, ozone treatment, heat treatment or the like), and since the technique is not a feature of the present invention, further detailed explanation is omitted.

Various natural substances (typically biological molecules such as DNA, RNA and other polynucleotides, oligopeptides, polypeptides, proteins, lipids, saccharides, and complexes of DNA with various organic polymers (such as polypeptides) or particulate metals and metal compounds or ceramics and other inorganic substances, or insoluble polymers and organic bodies) or artificially constructed substances (typically various artificial vectors, recombinant genes, liposomes, and artificial enzymes and other artificial proteins) can be adopted according to the object as the foreign substance to be introduced into target cells (plant cells and the like) in implementing the present invention. In particular, because the present invention is suited to obtaining plant cell and other transformants, a gene polynucleotide itself or various vectors constructed to include such a gene can be used favorably as the foreign substance.

In the method of the present invention, because a foreign substance can generally be introduced by physical means using a tiny hole (typically a hole with a diameter on a nanometer scale) generated in the cell wall of a target cell by the action of a cell wall-decomposing enzyme carried on a carbon nanotube, the foreign substance itself does not require any special pre-treatment, and can be pre-treated in accordance with conventional methods of introducing foreign substances into cells. For example, when using a gene consisting of DNA or RNA or a vector or other polynucleotide as the foreign substance, the foreign substance (and a solution or medium containing it) can be prepared as in conventional gene introduction methods such as microinjection and electroporation.

In addition to adjusting the conditions (pH, salt concentration, etc.) of the treatment object (cell suspension for example) for implementing the introduction method of the present invention so that the cell wall-decomposing enzyme can work efficiently and adding nutrients and chemicals necessary for the survival of the cells (various media, antibiotics, salts for pH adjustment or the like), it is desirable to include components that can improve the introduction efficiency of the foreign substance.

A typical example of this is a surfactant. A nonionic surfactant such as an alkyl glycoside, polyoxyethylene alkyl ether, polyoxyethylene alkyl phenol ether, polyoxyethylene fatty acid ester (polyethylene glycol), sucrose fatty acid ester, sorbitan fatty acid ester, fatty acid alkanolamide, polyvinyl alcohol or the like can be used by preference. Of these, it is particularly desirable to use an alkylglycoside, since these surfactants have relatively low molecular weights. Examples include n-octyl-β-D-glucoside, n-octyl-β-D-maltoside, n-decyl-β-D-maltoside, n-heptyl-β-D-thioglucoside and the like. A cationic surfactant such as an alkyltrimethyl ammonium salt, dialkyldimethyl ammonium salt, alkyldimethyl benzylammonium salt or amine salts can also be used. In addition to being added to the aforementioned treatment solution, these surfactants can also be used in preparing the aforementioned solution for introducing the foreign substance.

Consequently, these surfactants are preferably included as constituents of the foreign substance introduction kit provided by the present invention.

The foreign substance can be supplied directly to the treatment solution (that is, to the target cells), but it can also be supplied carried on (or contained in) a suitable introduction carrier, depending on the properties of the foreign substance. A carrier here is a medium for supplying (transporting) the foreign substance inside the cells. Examples include liposomes, particles and whiskers consisting of metals (gold, tungsten, etc.) and inorganic substances (such as silicon compounds), alginic acid beads, viral substances (such as coat proteins) and the like.

Consequently, a preferred embodiment of the foreign substance introduction kit provided by the present invention is one provided with at least one such introduction carrier.

A kit for introducing a specific foreign substance (for example, a kit already provided with a peptide (oligopeptide, polypeptide) or protein comprising a specific amino acid sequence or a polynucleotide comprising a specific nucleotide sequence or the like as the specific foreign substance) can also be provided by the present invention.

In addition to the primary constituent elements (enzymes, carbon nanotubes, surfactants, foreign substance and carrier as desired) discussed above, various reagents, solvents, tools (typically sterilized disposable tubes, dishes and other containers) and the like can be included in the kit provided by the present invention as shown in some of the examples below. These can be included as the kit as options, and the legal and technical scope of the kit of the present invention are not affected by the presence or absence of these accessory components and tools.

The foreign substance introduction method of the present invention is explained in more detail below by means of examples, but these examples are not intended to limit the present invention.

Example 1

In this example, a plant cell suspension derived from embryonic axes collected from the higher plant *Arabidopsis thaliana* was used for the target cells. This cell suspension was prepared as follows. MS medium (with 30 g/L saccharose and 0.2 g/L myoinositol added; same below) was used as the medium.

Sterilized *Arabidopsis thaliana* seeds were cultured (under dark conditions) on a plate containing 8 g/L agar-containing MS medium (pH 5.7), and after germination the embryonic axes were cut and harvested with a knife. The harvested embryonic axis tissue was then transferred to MS agar medium for callus culture, which was prepared by adding 8 g/L of agar to MS medium for callus culture (pH 5.7) containing 0.5 mg/L benzylaminopurine (BAP), 1 mg/L naphthalene acetic acid (NAA), 1 mg/L indoleacetic acid (IAA) and 1 mg/L 2,4-dichlorophenoxyacetic acid (2,4-D). Culture was then continued for about 4 weeks under dark conditions until callus formed. The resulting callus was subcultured every 4 weeks. Culture was performed under dark conditions at 23±1° C.

Next, about 1 g of callus was added to a 100 mL Erlenmeyer flask (triangular flask) containing 50 mL of the aforementioned MS medium for callus culture, and slowly rotated to break up the callus tissue and prepare a cell suspension. The culture flask was mounted on an orbital shaker, and rotation cultured at 100 rpm. Culture was performed under dark conditions at 23±1° C. The cell culture solution (suspension) was subcultured every 4 weeks.

Commercial cellulase was used as the cell wall-decomposing enzyme in this example. The Carbere® nanotubes mentioned above were purchased from the manufacturer and used as the carbon nanotubes. This carbon nanotube material also contains long-chain nanotubes a few μm to tens of μm in length, but the average chain length (total length) as determined by microscopic and AFM observation was about 0.5 μm. Cellulase-carrying carbon nanotubes were then prepared as follows.

First, 20 mg of the aforementioned carbon nanotubes were added to 60% nitric acid, and ultrasound treated for 30 minutes. This was followed by convection heating for 12 hours at 120° C. In this way, carboxyl groups were introduced as functional groups on the surface of the sample carbon nanotubes.

After completion of this heat treatment, the nanotubes were filtered with a polyacetate membrane with a pore diameter of 0.2 μm, and carbon nanotubes with introduced carboxyl groups were collected. The collected carbon nanotubes were washed 6 times with a suitable amount of pure water, and dried overnight at 80° C.

Next, 1 mg of carbon nanotubes with introduced carboxyl groups was mixed with 1 mL of MES (2-(N-Morpholino) ethanesulfonic Acid) buffer, and ultrasound treated for 10 minutes.

Next, 1 mL each of 400 mM EDC (1-(3-(dimethylamino) propyl)-3-ethylcarbodiimide hydrochloride) solution and 100 mM NHSS (N-hydroxysulfosuccinimide) solution were added to 1 mL of the aforementioned MES solution containing carbon nanotubes with introduced carboxyl groups, and agitated and mixed for 15 minutes. This served to activate the carboxyl groups on the surface of the carbon nanotubes. This was then centrifuged for 5 minutes at 15,000 rpm, and the supernatant was discarded. This mixing agitation and centrifugation in EDC and NHSS solution was repeated a total of 6 times.

Next, cellulase was fixed to the surface of the carbon nanotubes prepared in this way. Sigma Co. C1794-5KU was purchased and used as the cellulase.

Specifically, the carbon nanotubes were dispersed in 0.1 M phosphate buffer adjusted to pH 7. The previously purchased cellulase powder was then added to a concentration of 10 mg/mL. This was then agitated overnight at room temperature. In this way, "cellulase-carrying carbon nanotubes" were obtained having cellulase fixed to the surface of the carbon nanotubes by means of amide bonds formed between the carboxyl groups on the surface of the carbon nanotubes and amino groups in the cellulase molecules.

The next day, this dispersion was centrifuged for 7 minutes at 15,000 rmp, and the supernatant was discarded. Next, the centrifuged product (cellulase-carrying carbon nanotube fraction) was washed with Murashige and Skoog medium (hereunder called "MS medium"). This centrifugation treatment and washing treatment were repeated 4 times. Finally, 1 mL of MS medium containing 10% (w/v) n-octyl-$\beta$-D-glucoside was added to the centrifuged product to obtain a dispersion of cellulase-carrying carbon nanotubes (solution for foreign substance introduction). This dispersion was stored at 4° C., and was diluted with MS medium containing the surfactant n-octyl-$\beta$-D-glucoside for purposes of use.

The condition of the prepared cellulase-carrying carbon nanotubes was observed under an atomic force microscope (AFM). The curvature of the cantilever tip was 20 nm.

Figure 1B:
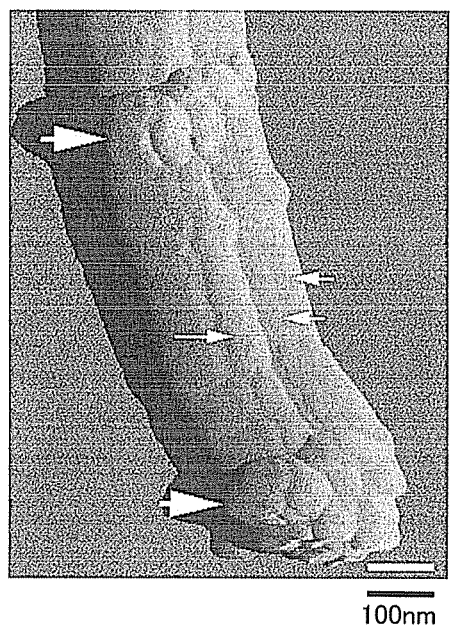
FIG. 1B is a photomicrograph showing the structure of a carbon nanotube after fixing of cellulase on the surface of the carbon nanotube in one example.

The results are shown in FIGS. 1A and 1B. FIG. 1A is a photomicrograph showing the carbon nanotubes before fixing of the cellulase, while FIG. 1B is a photomicrograph showing the prepared carbon nanotubes after fixing of the cellulase. The black arrows in the drawings indicate the structure of stacked open-bottom cups which is a feature of the Carbere® nanotubes used in this example. The small white arrows indicate carbon nanotubes, and the large white arrows indicate cellulase.

As shown by these figures, there is nothing adhering to the carbon nanotubes before preparation in FIG. 1A, but cellulase can be seen fixed to the surface of the carbon nanotubes in FIG. 1B.

Quantum dots about 1 to 10 nm in diameter (specifically, cadmium selenide (CdSe) particles) were used as the foreign substance. These quantum dots were purchased from Invitrogen.

Specifically, the purchased CdSe particles were reacted for 2 hours at 120° C. with trioctyl phosphine oxide (TOPO). They were then filtered with a 0.2 µm syringe filter. The filtered CdSe particles were added to a dispersion (solution for foreign substance introduction) containing 0.5 mg of cellulase-carrying carbon nanotubes, and left at room temperature for 2 hours. This was then centrifuged for 5 minutes at 15,000 rpm, and the supernatant was discarded. The centrifuged product was washed 4 times with MS medium, and the excess CdSe particles were removed to obtain cellulase-carrying carbon nanotubes with adsorbed CdSe particles (CdSe-containing solution for foreign substance introduction). These CdSe particles function as a fluorescence probe in cells, and when these particles have been successfully introduced into plant cells, they can be easily observed by fluorescence detection.

The cellulase-carrying carbon nanotubes with adsorbed CdSe particles prepared as described above (CdSe-containing solution for foreign substance introduction) were added to 10 mL of cell suspension containing 10% (w/v) OG. This was then cultured at 37°, and the condition of the cells was observed by fluorescence microscopy 1, 2, 3 and 5 hours after addition. A mercury lamp was used as the light source. The excitation wavelength was 480 nm.

Figure 2A:
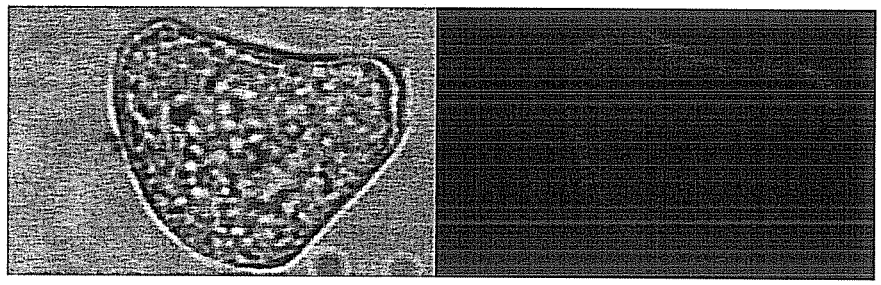
FIG. 2A is a photomicrograph showing the condition of a target plant cell after one hour following addition of a cellulase-carrying carbon nanotube in one example.
Figure 2B:
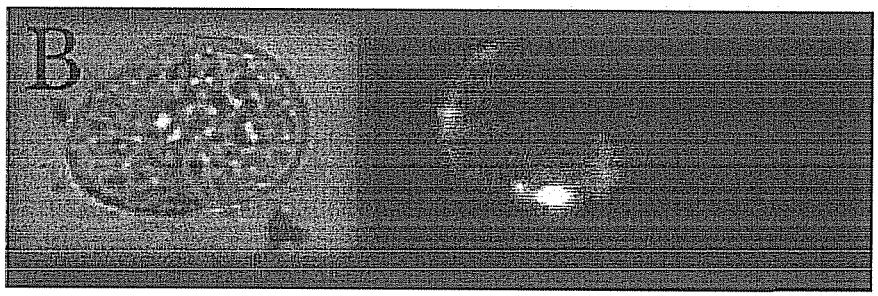
FIG. 2B is a photomicrograph showing the condition of a target plant cell after 2 hours following addition of a cellulase-carrying carbon nanotube in one example.
Figure 2C:
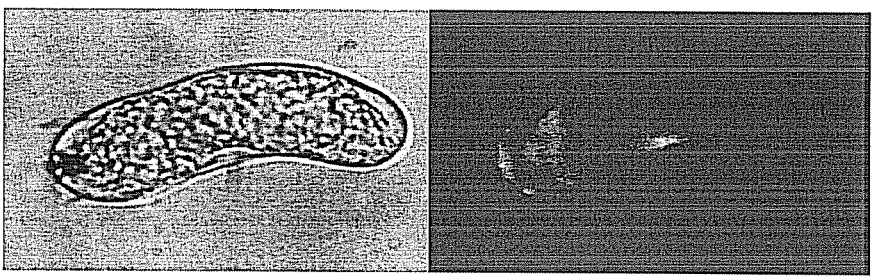
FIG. 2C is a photomicrograph showing the condition of a target plant cell after 3 hours following addition of a cellulase-carrying carbon nanotube in one example.
Figure 2D:
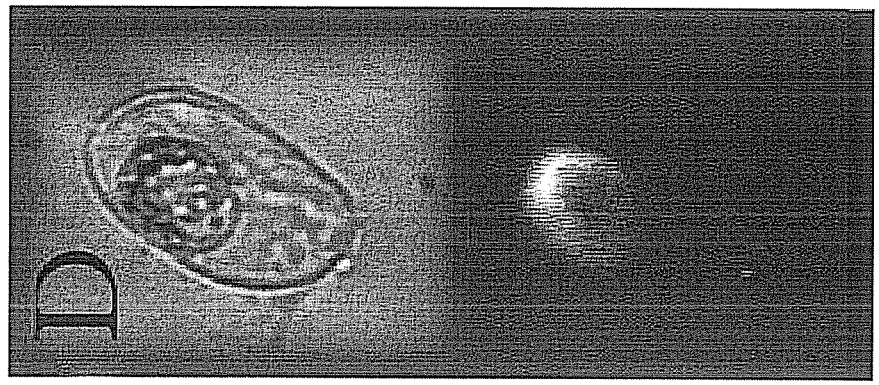
FIG. 2D is a photomicrograph showing the condition of a target plant cell after 5 hours following addition of a cellulase-carrying carbon nanotube in one example.

The results are shown in FIG. 2A through FIG. 2D. FIG. 2A shows the cells 1 hour after addition of carbon nanotubes, FIG. 2B shows the cells after 2 hours, FIG. 2C shows the cells after 3 hours and FIG. 2D shows the cells after 5 hours.

As shown by these images (photomicrographs), a hole can be opened in the cell wall of a target plant cell and a desired foreign substance (quantum dot in this case) rapidly and easily introduced into the cell using a cellulase-carrying carbon nanotube. 5 hours after addition of the cellulase-carrying carbon nanotubes, most of the quantum dots introduced into the cells were observed inside the vesicles (vacuoles).

Figure 3:
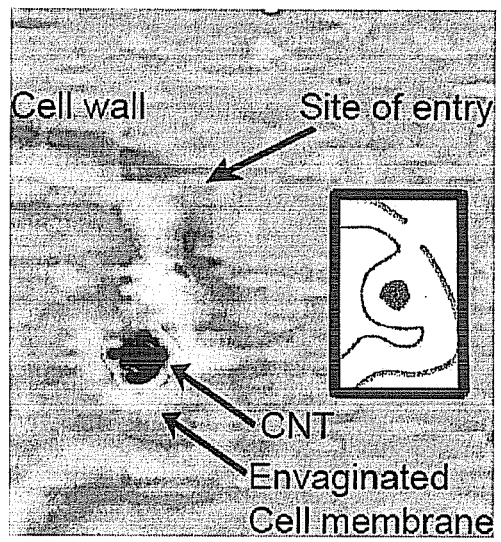
FIG. 3 is a photomicrograph (bright-field observation by transmitted illumination) showing a cellulase-carrying carbon nanotube penetrating the cell wall and being incorporated into the cell in one example.

As shown in FIG. 3, moreover, it was confirmed by microscopic observation (bright-field observation by transmitted illumination) that the cellulase-carrying carbon nanotubes used for treatment also passed through the cell wall and cell membrane to be incorporated into the cells. The data in the figure are from 30 seconds after addition of the cellulase-carrying carbon nanotubes. The carbon nanotubes incorporated into the cells were also observed to accumulate gradually in the vesicles (vacuoles).

However, there was no cell damage attributable to introduction of the carbon nanotubes, and introduction of the nanotubes themselves into the cells was not a problem from the standpoint of maintaining the cells.

In order to confirm that the results of FIGS. 2A through 2D were due to the cellulase activity of the carbon nanotubes, 200 mg of commercial cellulose powder (Sigma Co.) was added to 10 mL of the cellulase-carrying carbon nanotube dispersion prepared above (solution for foreign substance introduction), and agitated and mixed to prepare a cellulose treatment solution. The resulting treatment solution was incubated overnight at 37° C.

Figure 4:
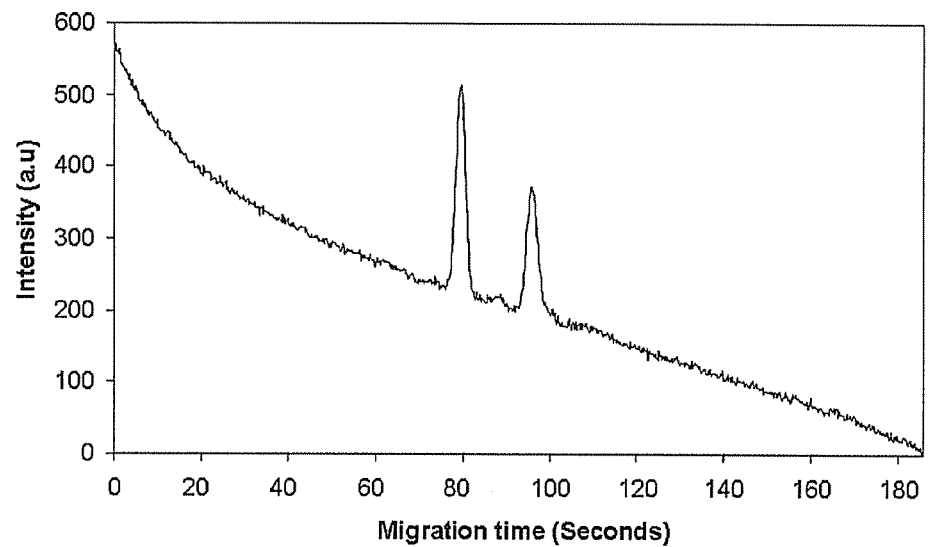
FIG. 4 is a graph showing the results of analysis of cellulose hydrolysates produced by the cellulase-carrying carbon nanotube of one example.

After completion of incubation, the cellulose treatment solution (hydrolysis solution) was investigated by electrophoresis using a Hitachi SV1100 unit. As shown by the graph of FIG. 4, the cellulose hydrolysis products glucose (Migration time: peak near 80 seconds in figure) and cellobiose (Migration time: peak near 100 seconds in figure) were detected. This shows that the cellulase carried (fixed) on the carbon nanotubes used in this example did not lose enzymatic activity, but maintained the ability to break down cellulose in the cell treatment solution (cell suspension).

Figure 5:
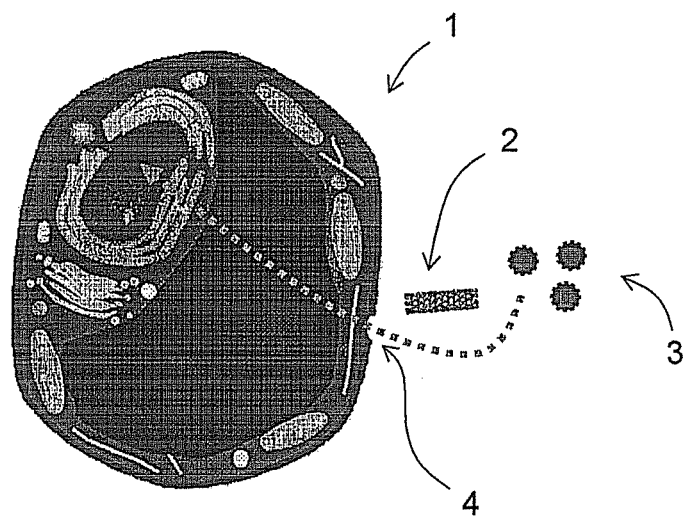
FIG. 5 is an explanatory diagram showing a model view of the introduction method of an example.

FIG. 5 is an outline of the foreign substance introduction method of the present invention. 1 indicates a plant cell, 2 a cellulase-carrying nanotube and 3 a quantum dot. This drawing shows how quantum dot 3 and carbon nanotube 2 are introduced into plant cell 1 through tiny hole 4 formed by cellulase fixed on the carbon nanotube.

The effects of the surfactant n-octyl-$\beta$-D-glucoside (hereunder called "OG") and the cell wall-decomposing enzyme cellulase on introduction efficiency when introducing a foreign substance into a target plant cell (*Arabidopsis thaliana*) were investigated.

Cellulase-carrying carbon nanotubes with adsorbed CdSe particles prepared as described above (CdSe-containing solution for foreign substance introduction) were added to OG-containing cell suspensions of different concentrations ranging from 0.75% (w/v) through 15% (w/v), and cultured for 3 hours at 25° C. The introduction rate into the various plant cells was investigated after culture. The introduction rate using carbon nanotubes without cellulase was also investigated in the same way. The results are shown in Table 1.

TABLE 1

| CSCNT-cellulase concentration [μg/mL] | OG concentration [% (w/v)] | Cell count in cell suspension | Number of cells with introduced particles | Introduction rate [%] |
|---|---|---|---|---|
| 100 | — | 100 | 3 | 3 |
| 100 | 0.75 | 123 | 8 | 6.5 |
| 100 | 6 | 97 | 10 | 10.3 |
| 100 | 10 | 109 | 22 (through 15 fluorescent particles/cell) | 20.2 |
| 100 | 15 | 97 | 17 | 17.5 |
| 200 | — | 103 | 5 | 4.8 |
| 100 (cellulase not attached) | 10 | 100 | 9 (1-2 fluorescent particles/cell | 9 |
| | — | 93 | 0 | 0 |

As shown by the results of Table 1, the higher the OG concentration of the OG-containing cell suspension (hereunder called rate "OG solution"), the greater the introduction rate.

The introduction rate was greatest after addition to a 10% (w/v) OG solution, at 20.2%. The introduction rate after addition to a 15% (w/v) OG solution (17.5%) was lower than after addition to a 10% (w/v) OG solution. The introduction rate was much lower (3%) when introduction was attempted with a cell suspension containing no OG.

Using a cell suspension containing no OG and carbon nanotubes with no attached cellulase, the introduction rate was 0%, while on the other hand the introduction rate was 9% in the case of addition to an OG solution containing 10% (w/v) OG using carbon nanotubes without attached cellulase. This shows that the presence of OG and cellulase and particularly the presence of OG is important for efficient introduction of a foreign substance into a plant cell. It was also shown that the introduction rate is dependent on the concentration of the OG solution.

0.75% (w/v), 6% (w/v) and 10% (w/v) OG solutions containing no cell suspension were also prepared, cellulase-carrying carbon nanotubes (solution for foreign substance introduction) were added to each OG solution, and the status of the carbon nanotubes was observed and photographed under an electron microscope.

The result (not shown) was that while almost no random movement of the carbon nanotubes was observed after addition to a 0.75% (w/v) OG solution, translation, rotation and other Brownian movement of the carbon nanotubes occurred after addition to the 6% (w/v) and 10% (w/v) OG solutions. This movement was also found to be more active after addition to the 10% (w/v) OG solution.

This confirms that the random movement of cellulase-carrying carbon nanotubes can be further promoted by adding an OG solution in advance to cell culture liquid or cellulase-carrying carbon nanotubes (solution for foreign substance introduction).

Example 2

In this example, a cell suspension derived from embryonic axes collected from the higher plant *Arabidopsis thaliana* was used for the target cells. This cell suspension was prepared as in Example 1 above.

2.5 mg of cellulase-carrying carbon nanotubes prepared as in Example 1 were added to 2.5 mL of MS medium containing 10% (w/v) n-octyl-β-D-glucoside to obtain the cellulase-carrying carbon nanotube dispersion of this example.

The resulting dispersion was allotted to 5 petri dishes 3.5 cm in diameter. 0.5 mL of the aforementioned cell suspension was added to each Petri dish, and mixed carefully.

In this example, a commercial plant cell DNA vector (Clontech pBI vector, pBI121 in this case) containing the neomycin phosphotransferase II gene and the galactosidase gene was used as the foreign substance.

Specifically, this DNA vector was diluted with MS medium, and added to each Petri dish to obtain 5 DNA concentrations of 2.5 μg/mL, 5 μg/mL, 7.5 μg/mL, 10 μg/mL and 12.5 μg/mL.

The cell suspension (treatment solution) having carbon nanotubes and a DNA vector added thereto as described above was cultured for 3 hours at 25° C.

After completion of culture, the cells in the suspension were transferred to MS medium containing 1 mg/mL of 2,4-dichlorophenoxy acetic acid (2,4-D; synthetic auxin) and 0.5 mg/mL of kinetin ($N^6$-furfuryladenine; cytokinin analog) and cultured for 24 hours at 25° C.

Next, the cells were collected and the collected cells were further cultured at 25° C. in MS medium containing 2,4-D or kinetin in the above concentration as well as 50 μg/L of kanamycin.

Forty days after the start of culture in the kanamycin-containing MS medium, the survival of the cultured cells was confirmed. This shows that that DNA vector was introduced into the plant cells in the culture, and the kanamycin resistance gene (neomycin phosphotransferase II gene) contained in the vector was expressed. Consequently, it is also shown by this example that with the method of the present invention it is possible to easily and conveniently introduce a desired foreign substance (particular a gene or other biological molecule) into plant cells. This example also shows that transformed plant cells can be easily obtained by applying the introduction method of the present invention.

Example 3

In this example, a commercial DNA vector for plant cells (Invitrogen pBI vector, the pBI-GW-NOS vector in this case) containing a GFP (Green Fluorescent Protein) expression gene was used as the foreign substance. Apart from the change in a foreign substance, the cell suspension derived from embryonic axes collected from *Arabidopsis thaliana* and the cellulase-carrying carbon nanotubes were prepared by methods similar to those of Example 1.

Specifically, the pBI-GW-NOS vector was added to a concentration of 750 ng/μL to a solution for foreign substance introduction containing 10 μg of cellulase-carrying carbon nanotubes, and left for 2 hours at 25° C. Next, this solution was added to 10 mL of a cell suspension (containing 10 cells per 1 containing 10% (w/v) OG, and cultured at 25° C.

Figure 6:
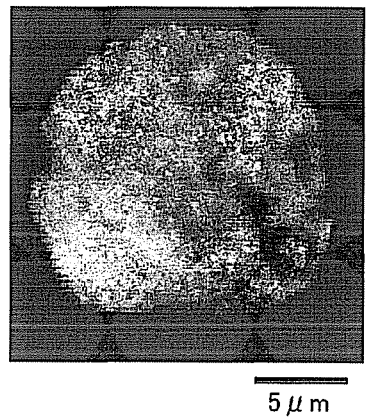
FIG. 6 is a three-dimensional reconstruction of a target plant cell having a foreign substance incorporated therein in one example.

After 48 hours of culture, GFP expression was confirmed. FIG. 6 shows a three-dimensional reconstruction of an *Arabidopsis thaliana* cell after culture.

As shown by FIG. 6, expression of GFP emitting green light was confirmed in the *Arabidopsis thaliana* cells. The presence of multiple carbon nanotubes was also confirmed in the cells. This shows that the pBI-GW-NOS vector was introduced, and the GFP contained in this vector was expressed. The average introduction rate was 6% in this example.

Consequently, it was also confirmed from this example that a hole can be opened in the cell wall of a target plant cell and a desired foreign substance rapidly and easily introduced into the cell using cellulase-carrying carbon nanotubes according to the method of the present invention. This example also shows that a transformed plant cell can be easily obtained by implementing the introduction method of the present invention.

Example 4

In this example, introduction of cellulase-carrying carbon nanotubes into cells was attempted using for the target cells a cell suspension derived from embryonic axes collected from another higher plant, *Glycyrrhiza glabra* in the legume family. This cell suspension was prepared as follows. Linsmaier and Skoog medium (hereunder called "LS medium") was used as the medium. Although the target cells were different, the cellulase-carrying carbon nanotubes and foreign substance were prepared by methods similar to those used in Example 1.

That is, embryonic axis tissue collected from sterilized *Glycyrrhiza glabra* seeds was transferred to LS agar medium for callus culture, which was prepared by adding agar to LS medium for callus culture (pH 5.8) containing 0.1 mM naphthalene acetic acid (NAA) and 1 μM benzyl adenine (BA). Culture was then continued for about 3 weeks under dark conditions until callus formed. The resulting callus was then subcultured every 3 weeks. Culture was performed under dark conditions at 25° C.

Next, the callus was added to 25 mL of the aforementioned LS medium for callus culture, and rotated slowly to break up the tissue and prepare a cell suspension. Culture was performed under dark conditions at 25° C. The cell culture liquid (suspension) was subcultured every 4 weeks.

Cellulase-carrying carbon nanotubes with adsorbed CdSe prepared by the same methods as in Example 1 (CdSe-containing solution for foreign substance introduction) were added to 10 mL of cell suspension containing 10% (w/v) OG, and cultured for 8 hours at 25° C.

Figure 7A:
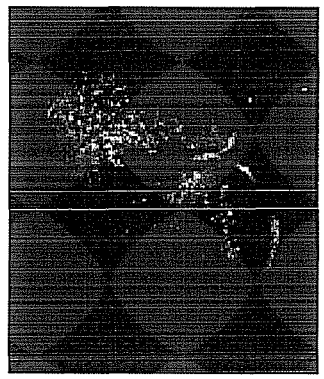
FIG. 7A is a fluorescence micrograph showing the inside of a target cell after introduction of a foreign substance (observation of cellulase-carrying carbon nanotube).
Figure 7B:
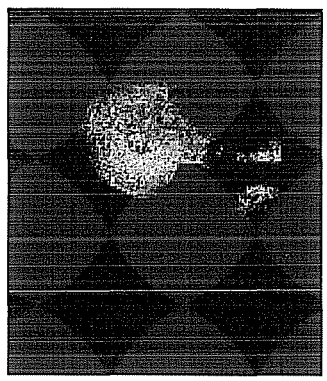
FIG. 7B is a fluorescence micrograph showing the inside of a target cell after introduction of a foreign substance (observation of nucleic acid).
Figure 7C:
FIG. 7C is a fluorescence micrograph showing the inside of a target cell after introduction of a foreign substance (observation of cellulase-carrying carbon nanotube and nucleic acid).
Figure 7D:
FIG. 7D is a fluorescence micrograph showing the inside of a target cell after introduction of a foreign substance (bright-field observation of cellulase-carrying carbon nanotube and nucleic acid).

After culture, the condition of the cells was observed by fluorescence microscopy. The photographs taken during this observation are shown in FIG. 7A through FIG. 7D. The same visual field was photographed in all cases. FIG. 7A is a photograph of a cellulase-carrying carbon nanotube with adsorbed CdSe emitting green light. FIG. 7B is a photograph of the nucleic acid of a target cell stained with DAPI. FIG. 7C is a photograph of a cellulase-carrying carbon nanotube and nucleic acid. FIG. 7D is a bright-field observation photograph by transmitted illumination.

As shown by these FIG. 7A through FIG. 7D, many cellulase-carrying carbon nanotubes emitting green light were confirmed within the cells and particularly within the nuclei. This shows that the cellulase-carrying carbon nanotubes were transported into the vesicles (vacuoles), and were also found in the nuclei. Consequently, it was confirmed that a hole can be opened in the cell wall of the target *Glycyrrhiza glabra* plant cell and a desired foreign substance rapidly and easily introduced inside the cell using a cellulase-carrying carbon nanotube according to the present invention. This example also shows that a transformed plant cell can be easily obtained by applying the introduction method of the present invention.

Thus, with the present invention it is possible to easily and conveniently introduce a foreign substance into a cell having a cell wall (particularly a plant cell) by using a cell wall enzyme-decomposing enzyme-carrying carbon nanotube in place of conventional methods of foreign substance introduction, which are complicated and inefficient.

It is also possible to easily obtain a target transformant by introducing as the foreign substance a gene (polynucleotide) or gene construct (vector or the like) that is capable of expression in the target cell.

INDUSTRIAL APPLICABILITY

The method of the present invention is not limited to the test examples given above, but can be applied favorably for example to the manufacture of small capsules, in which the enclosed substance is a low-molecular-weight substance, such as polynucleotides other than plasmid DNA (antisense oligo-DNA, RNA, etc.), proteins (enzymes and the like), or a functional peptide, oligosaccharide or the like. Like the microchips used in conventional methods, the base materials used in the present invention are easy to mass-produce.

The invention claimed is:

1. A method for introducing a foreign substance into a plant cell having a cell wall, the method comprising:
   preparing short-chain carbon nanotubes with an average length of 1 μm or less carrying at least one kind of cellulase that is chemically bound to the carbon nanotubes;
   preparing a foreign substance to be introduced into a plant cell, wherein the foreign substance is separately prepared from the cellulase-carrying nanotubes;
   supplying the cellulase-carrying carbon nanotubes and the foreign substance to a treatment object containing the plant cell;
   forming a nano-hole in the cell wall of the plant cell by an action of the cellulase carried on the carbon nanotubes upon contact of the carbon nanotubes with the plant cell; and
   introducing the cellulase-carrying carbon nanotubes together with the foreign substance into the plant cell through the nano-hole in the cell wall;
   wherein the foreign substance is selected from the group consisting of polynucleotides, oligopeptides, polypeptides, proteins, lipids, saccharides, complexes of DNA with polypeptides, particulate metals or metal compounds, and ceramics.

2. The method according to claim 1, wherein the prepared cellulase-carrying carbon nanotube is added in advance to a solution containing a surfactant to prepare a solution for foreign substance introduction, and this prepared solution is supplied to a treatment object containing the plant cell.

3. The method according to claim 1, wherein the cell treatment object is a treatment solution containing the plant cell, and this cell treatment solution contains a surfactant.

4. The method according to claim 1, wherein the cell treatment object is a treatment solution containing the plant cell, and this cell treatment solution contains a surfactant.

5. The method according to claim 2, wherein n-octyl-β-D-glucoside is used as the surfactant.

6. The method according to claim 3, wherein n-octyl-β-D-glucoside is used as the surfactant.

7. The method according to claim 1, wherein a polynucleotide is introduced as the foreign substance.

\* \* \* \* \*